United States Patent [19]

Baba et al.

[11] Patent Number: 4,619,614

[45] Date of Patent: Oct. 28, 1986

[54] ROTATIONAL COUPLING DEVICE FOR A DENTAL HANDPIECE HAVING A BUILT-IN BATTERY

[75] Inventors: Tadashi Baba, Kanuma; Norimasa Kaneko, Utsunomiya, both of Japan

[73] Assignee: Nakanishi Dental Mfg. Co., Ltd., Kanuma, Japan

[21] Appl. No.: 646,211

[22] Filed: Aug. 31, 1984

[30] Foreign Application Priority Data

Sep. 1, 1983 [JP] Japan .......................... 58-135805[U]

[51] Int. Cl.⁴ ............................................... A61C 1/02
[52] U.S. Cl. ...................................... 433/99; 433/126; 433/131
[58] Field of Search .......................... 433/99, 126, 131

[56] References Cited

U.S. PATENT DOCUMENTS 3,848,336 11/1974 Copeland ............................... 433/99
3,921,298 11/1975 Fattaleh .................................. 433/99

FOREIGN PATENT DOCUMENTS 3122062 2/1982 Fed. Rep. of Germany ........ 433/99
3122065 3/1982 Fed. Rep. of Germany ........ 433/99

*Primary Examiner*—John J. Wilson
*Attorney, Agent, or Firm*—Wenderoth, Lind & Ponack

[57] ABSTRACT

A rotational coupling device for a cordless dental instrument including a motor housing which has a pair of semi-annular projections integrally provided at a rear end thereof with a pair of arc-shaped recesses formed between the coupling projections and semi-annular slot provided around the inner peripheries of the semi-annular projections. A battery housing has a pair of semi-annular around an outer periphery adjacent its front end, a pair of arc-shaped projections coinciding with the arc-shaped recesses of the motor housing and a pair of semi-annular flanges coinciding with the pair of semi-annular projections of the motor housing so as to form a rotational coupling between the motor housing and the battery housing. An insulating disc having a pair of contacts connected to a motor fits into a rear opening of the motor housing. Another insulating disc having a pair of arc-shaped guide slots fits into a forward opening of the battery housing, each slot including a positive contact, a negative contact and a neutral non-contact point which are selectively connected to the pair of contacts of the motor housing. The motor housing has a standard marking, which is rotatably aligned with a normal marking, a reverse marking and a neutral, marking on the battery housing to drive the drive motor in a normal direction, in a reverse direction or to stop the motor, respectively.

3 Claims, 6 Drawing Figures

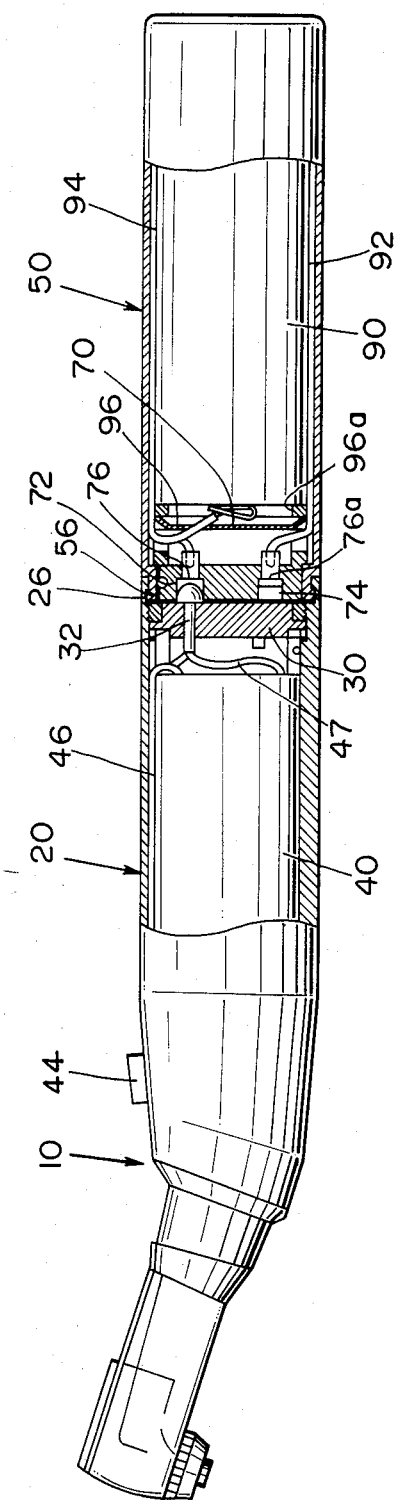

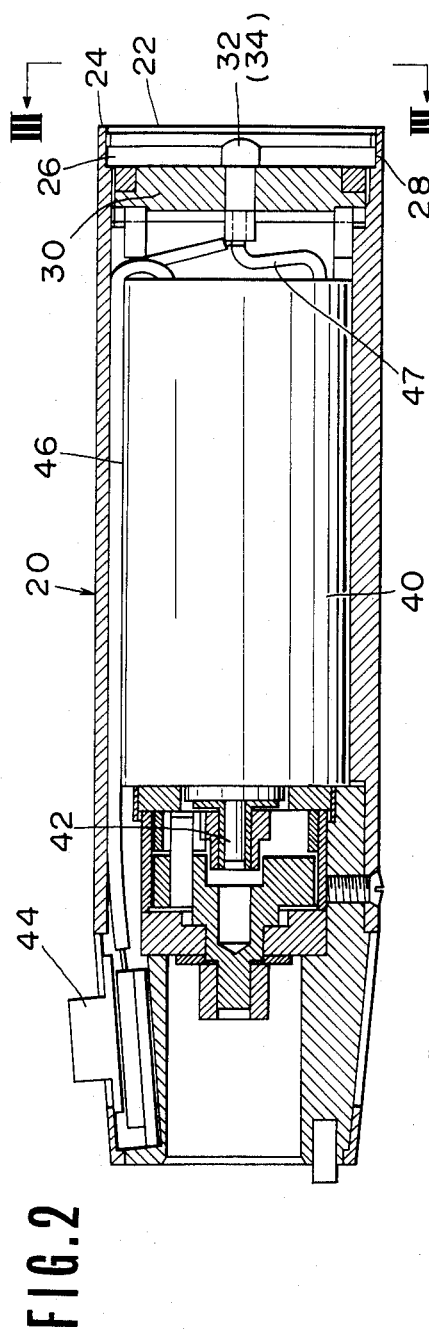
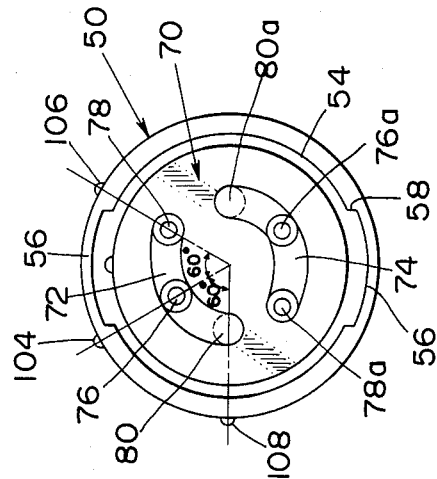
FIG.5
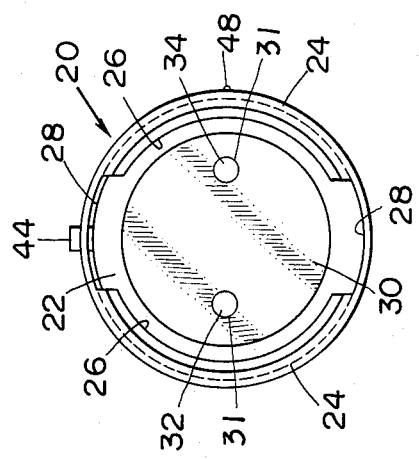
FIG.3
FIG.2

ROTATIONAL COUPLING DEVICE FOR A DENTAL HANDPIECE HAVING A BUILT-IN BATTERY

BACKGROUND OF THE INVENTION

This invention relates to improvements in a cordless rotational coupling device for a dental instrument having a built-in battery which enables a dentist to disconnect a battery housing from a motor housing or to rotatably join them easily and quickly.

In the dental handpiece having a built-in battery, it has been necessary to disconnect the built-in battery independently of a drive motor in order to either charge the battery or to exchange the worn out battery with a new one. The coupling device between the motor housing and the battery housing is so complicated that it is very difficult to disassemble or assemble them quickly.

OBJECTS OF THE INVENTION

A principal object of this invention is to provide a rotational coupling device for a dental handpiece whereby a built-in battery can be either disconnected from a motor housing or rotatably joined to the motor housing quite easily and quickly to facilitate disconnection of the built-in battery for its charging, reparing or exchanging.

Another object of this invention is to provide a rotational coupling device for a dental handpiece having a built-in battery whereby contacts for a change-over switch can be easily selected for normal and reverse rotations of a drive motor or for its stop by selectively turning a battery housing with respect to a motor housing.

Another object of this invention is to provide a rotational coupling device for a dental handpiece having a built-in battery whereby a battery housing can be electrically securely coupled to a motor housing during use.

A further object of this invention is to provide a dental handpiece which can be easily assembled or disassembled.

Still another object of this invention is to provide a device suitable for the aforementioned purposes which will have a comparatively simple construction and at the same time be sufficiently rigid, strong and durable.

BRIEF DESCRIPTION OF DRAWING

While we have shown in the accompanying drawings, a preferred embodiment of our invention, it should be understood that the same is susceptible of modification and change without departing from the spirit of our invention.

FIG. 1 is an exploded side elevational view, partially broken away, of the dental handpiece of this invention;

FIG. 2 is a greatly enlarged detailed vertical sectional view of a motor housing of the dental handpiece shown in FIG. 1;

FIG. 3 is a front elevation taken in the direction of line III—III of FIG. 2;

FIG. 5 is a front elevation taken in the direction of line V—V of FIG. 4; and

DETAILED DESCRIPTION OF THE PREFERRED EMBODIMENT

Figure 4:
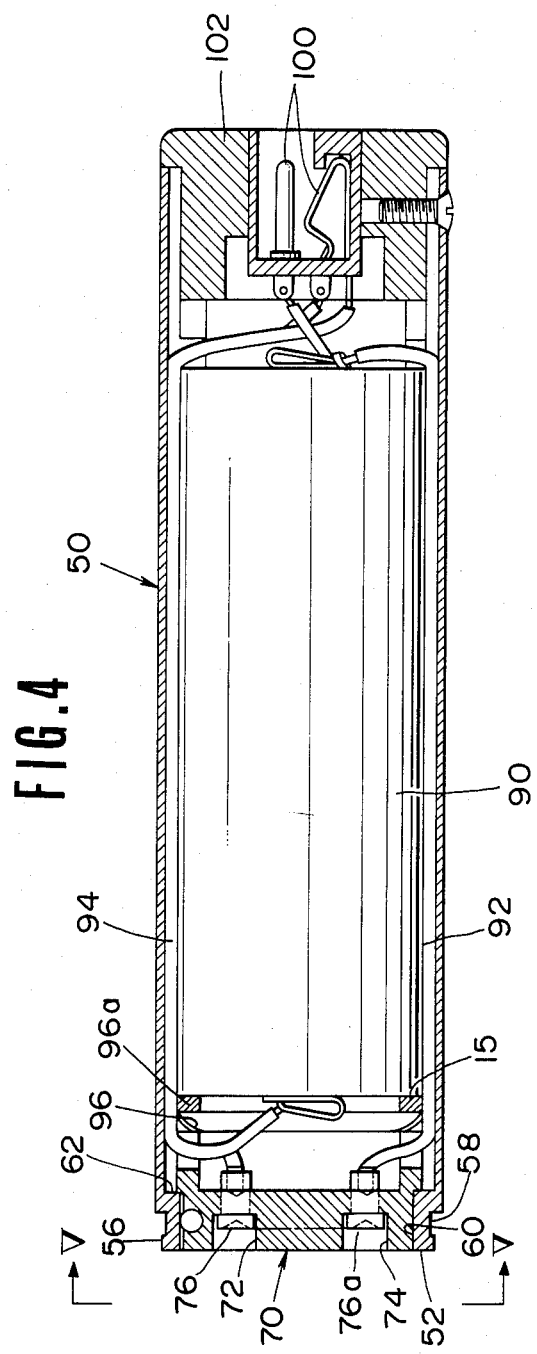
FIG. 4 is a greatly enlarged detailed vertical sectional view of a battery housing of the dental handpiece shown in FIG. 1.

Referring to the accompanying drawings, the dental handpiece 10 of this invention comprises a motor housing 20 and a battery housing 50 which is detachably coupled into a rear end portion opening 22 of the motor housing 20.

A d.c. motor 40 which is arranged in position in the motor housing 20 is connected by a lead wire 46 to a switch 44 which projects through the motor housing at its front portion. A drive shaft 42 of the motor 40 is axially arranged so that it can be coupled to a rear end portion of a driven shaft (not shown).

A pair of semi-annular projections 24 having a pair of arc-shaped upper and lower recesses 28, extend into a circular opening in a rear portion of the motor housing 20, both peripheral recesses 28 being symmetrical with the center of the rear end opening 22 of the motor housing 20. A pair of semi-annular slots 26 (as shown in FIG. 3) are provided around an inner periphery of the motor housing 20 adjacent a rear side of the semi-annular projections 24.

A circular insulating disc 30 having a pair of diametrically opposed apertures 31 which are symmetrical with respect to its center is fitted into the rear end opening 22 of the motor housing 20. A pair of positive and negative contacts 34 and 32, respectively of both lead wires 46 and 47, extend from a rear end portion of the motor 40. Each contact is threaded through one of the apertures 31 to extend slightly out of the rear end wall of the insulating disc 30.

As shown in FIGS. 4 and 5, the battery housing 50 is provided with a small diameter front inlet portion 60 at its front end portion 52.

A pair of semi-annular slots 58 is provided around an external periphery of a pair of arc shaped projections 56 of the battery housing 50 adjacent its front end portion 52. The pair of arc-shaped upper and lower projections 56, coinciding with the arc-shaped upper and lower recesses 28, are provided at a front end peripheral inlet portion 52. Accordingly, a pair of semi-annular remaining dent flanges 54 correspond to the semi-annular projections 24 of the motor housing 20, thus forming a rotational coupling between the motor housing 20 and the battery housing 50.

An insulating disc 70 having a diameter to fit into a small diameter front inlet portion 60 is axially provided with a pair of arc-shaped guide slots 72 and 74 which are symmetrical with the center of the disc 70. A positive contact 76 is provided at a central portion of the slot 72, with a negative contact 78 being at a right end portion and a neutral non-contact point 80 at a left end portion respectively. In a similar manner, a negative contact 76a is located at a central portion of the slot 74, with a positive contact 78a being at a left end portion and a neutral point 80a at a right end portion respectively.

A radially stepped peripheral portion of the insulating disc 70 is to be engaged with a radially stepped portion 62 of the battery housing 50 when the disc 70 is introduced into the battery housing 50.

A lead wire 92 extending from a negative contact of the battery 90 is connected to the negative contacts 78 and 76a respectively, while a lead wire 94 extending from a positive contact of the battery 90 is connected to the positive contacts 76 and 78a respectively.

The charging battery 90, which is connected to the positive contacts 76 and 78a and the negative contacts 78 and 76a respectively, is arranged in position in the battery housing 50 to locate the insulating disc 70 at the front inlet portion 60, and a plate spring 96 is interposed between the insulating disc 70 and the front end portion of the battery 90, with a support 96a being arranged between the plate spring 96 and the front end portion of the battery 90 so as to urge said insulating disc forwardly.

Both ends of the lead wires 92 and 94 are respectively connected to charging contacts 100, which are arranged in a fitting connection 102 located at a rear end inlet portion of the battery housing 50. The charging contacts 100 form a plug which is inserted into a socket (not shown) for charging.

Figure 6:
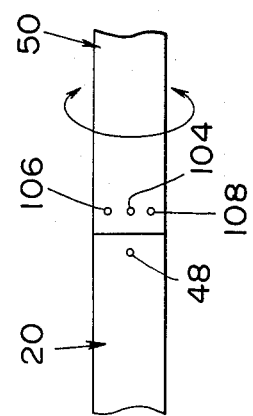
FIG. 6 is an elevational view in section of the coupled portions between the motor housing and the battery housing of the dental handpiece of this invention, particularly having markings for a change-over switch.

As shown in FIG. 6, a standard marking 48 is provided on the outer periphery of the motor housing 20 adjacent its rear end portion, a normal turning marking 104, for indicating a connection between contacts 32,34 and the positive contact 76 and the negative contact 76a, is provided on the outer periphery of the battery housing 50 adjacent its front end portion which coincides with the standard marking 48. The normal turning marking indicates that the drive motor will rotate in a normal direction. A reverse marking 106 and a neutral non-contact point marking 108 are each provided along the circumference battery housing of on either side of the normal turning marking at an angular displacement of 60° relative to the normal turning marking 104. The reverse marking 106 indicates connection of the negative contact 78 and the positive contact 78a for driving the motor 40 to rotate in the opposite direction, and the neutral marking 108 shows the non-contact point between the contacts of the motor 40 and those of the battery 96, thus causing the drive motor to stop.

While an embodiment of the invention has been described, it is obvious that variations and modifications are possible without departing from the invention. It is desired to cover all such forms of the invention as would be apparent to one skilled in the art, and that come within the scope of the appended claims.

We claim:

1. A rotational coupling device for a cordless dental instrument comprising:
   a motor housing and a battery housing which are detachably coupled together;
   a direct current motor mounted in said motor housing and a charging battery mounted in said battery housing;
   switch means, operatively connected to said direct current motor and mounted on said motor housing, for manually activating and deactivating said direct current motor;
   said motor housing having a rear end with a circular opening therein, a pair of semi-annular projections extending radially into said circular opening and a pair of arc-shaped recesses formed between the ends of said semi-annular projections;
   a first insulating disc disposed in said circular opening and having two symmetrical, diametrically opposed apertures, each aperture having a lead wire extending therethrough, an end of said lead wire connected to said switch and an end of the other said lead wire connected to said motor, the other end of each said lead wire connected to a contact on said first insulating disc which projects from a surface of said first insulating disc facing said battery housing;
   said battery housing having a forward end with a circular inlet therein, a pair of arc-shaped projections extending radially outward from said circular inlet and adapted to fit in said arc-shaped recesses in said motor housing, a pair of semi-annular flanges formed between said pair of arc-shaped projections and adapted to fit in said semi-annular projections of said motor housing, said arc-shaped projections being rotatable in said circular opening of said motor housing for engaging said semi-annular projections of said motor housing and detachably coupling said motor housing to said battery housing;
   a second insulating disc disposed in said circular inlet of said battery housing and having two symmetrical, diametrically opposed arc-shaped guide slots which are adapted to receive said projecting contacts on said first insulating disc, one of said guide slots having a centrally disposed positive contact with a neutral and negative contact on either side thereof, the other of said guide slots having a centrally disposed negative contact with a positive and neutral contact on either side thereof, said neutral contacts being diametrically opposed to each other and said positive contacts being diametrically opposed to said negative contacts, said second insulating disc having a radially stepped peripheral portion engaged with a radially stepped portion of said battery housing for retaining said second insulating disc in said battery housing;
   a lead wire connected between said negative contacts in said guide slots and a negative terminal of said charging battery, another lead wire connected between said positive contacts in said guide slots and a positive terminal of said charging battery; and
   a positive and negative charging contact disposed on a rear end of said battery housing, each of which is connected to a respective positive and negative terminal of said charging battery.

2. The rotational coupling device for a cordless dental instrument of claim 1, wherein a plate spring is disposed in said battery housing between said second insulating disc and said charging battery and a support is disposed in said battery housing between said charging battery and said plate spring for urging said second insulating disc towards said forward end of said battery housing.

3. The rotational coupling device for a cordless dental instrument of claim 1, wherein said motor housing has a standard marking on an exterior surface adjacent said rear end thereof, said battery housing has a circumferential row of three markings on an exterior surface adjacent said forward end thereof which selectively align with said standard marking, said three markings corresponding to positions at which said contacts on said first insulating disc engage diametrically opposed contacts on said second insulating disc corresponding to normal rotation of said motor, reverse rotation of said motor and stopped rotation of said motor, respectively.

* * * * *